(12) United States Patent
Guth et al.

(10) Patent No.: US 10,126,275 B2
(45) Date of Patent: Nov. 13, 2018

(54) DOUBLE-WALL INLET LINERS FOR GAS CHROMATOGRAPHY

(71) Applicant: Cyclone Biosciences LLC, Phoenix, AZ (US)

(72) Inventors: Jason Guth, Tempe, AZ (US); Stephen E. Griffin, Peoria, AZ (US); Brian Barr, Scottsdale, AZ (US)

(73) Assignee: Cyclone Biosciences LLC, Phoenix, AZ (US)

(*) Notice: Subject to any disclaimer, the term of this patent is extended or adjusted under 35 U.S.C. 154(b) by 187 days.

(21) Appl. No.: 15/289,241

(22) Filed: Oct. 10, 2016

(65) Prior Publication Data

US 2017/0108475 A1   Apr. 20, 2017

Related U.S. Application Data

(60) Provisional application No. 62/242,279, filed on Oct. 15, 2015.

(51) Int. Cl.
*G01N 30/16* (2006.01)
*G01N 30/60* (2006.01)
*G01N 30/12* (2006.01)

(52) U.S. Cl.
CPC .......... *G01N 30/16* (2013.01); *G01N 30/12* (2013.01); *G01N 2030/126* (2013.01)

(58) Field of Classification Search
CPC .. G01N 30/12; G01N 30/16; G01N 2030/126; G01N 30/6078; G01N 30/6004; G01N 30/10; G01N 2030/167; G01N 30/60

USPC .......................................................... 96/105
See application file for complete search history.

(56) References Cited

U.S. PATENT DOCUMENTS

| | | |
|---|---|---|
| 4,035,168 A | 7/1977 | Jennings |
| 5,119,669 A | 6/1992 | Silvis et al. |
| 6,203,597 B1 * | 3/2001 | Sasano .................... G01N 30/12 95/87 |
| 6,929,780 B2 | 8/2005 | Gerstel |
| 7,469,557 B2 | 12/2008 | Griffin et al. |
| 8,366,814 B2 | 2/2013 | Jones et al. |
| 8,713,989 B2 | 5/2014 | Pa et al. |
| 8,845,794 B2 | 9/2014 | Klee |
| 8,999,044 B2 | 4/2015 | Rohland et al. |
| 2012/0204621 A1 * | 8/2012 | Rohland ................. G01N 30/16 73/23.41 |

* cited by examiner

*Primary Examiner* — Robert Clemente
(74) *Attorney, Agent, or Firm* — Synthesis IP

(57) ABSTRACT

Herein is disclosed an inlet liner for use within an injection port of a capillary gas chromatograph. The inlet liner can include a first fused quartz tube and a second fused quartz tube aligned along a common longitudinal axis; the outside surface of the first fused quartz tube affixed to the inside surface of the second fused quartz tube. In certain instances, the tubers are affixed at two points along the longitudinal axis thereby defining a hermetically sealed volume between the outside surface of the first quartz tube and the inside surface of the second fused quartz tube, wherein the hermetically sealed volume entrains a reactive surface.

8 Claims, 9 Drawing Sheets

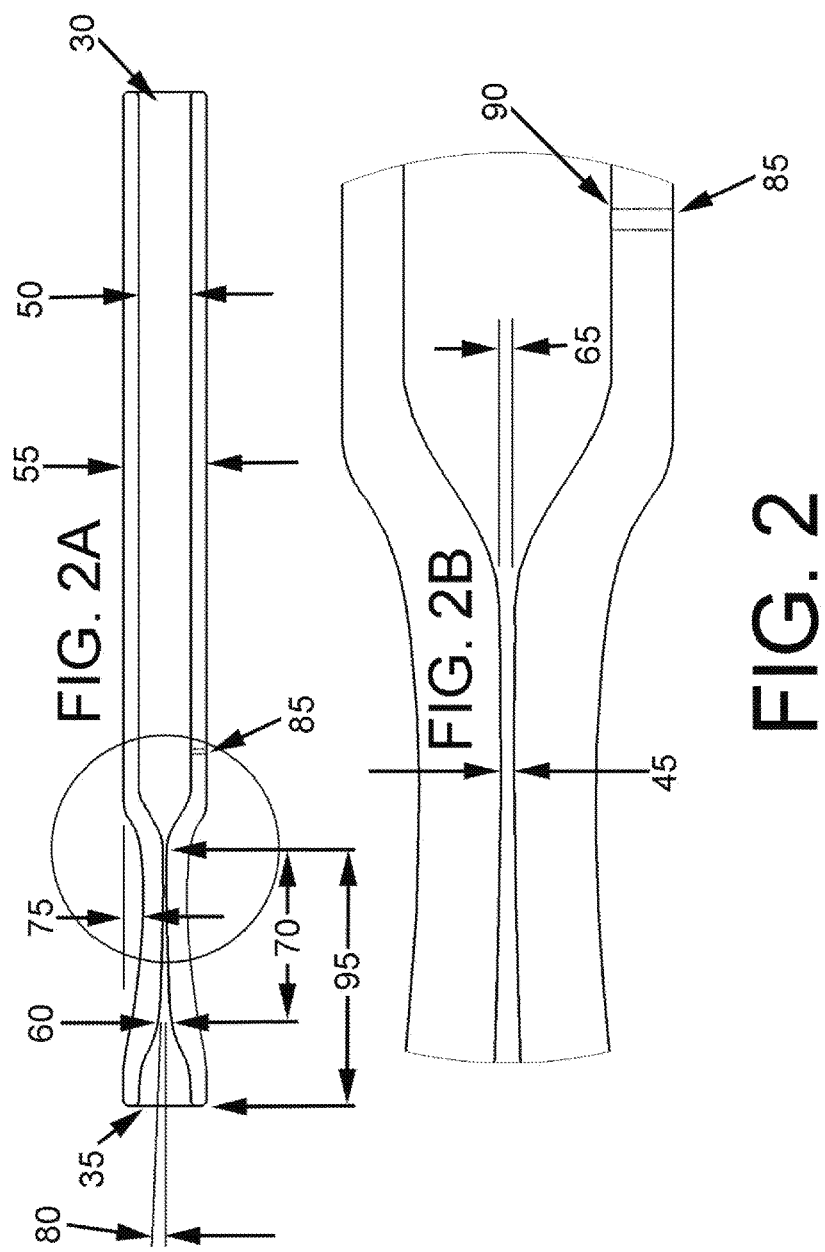

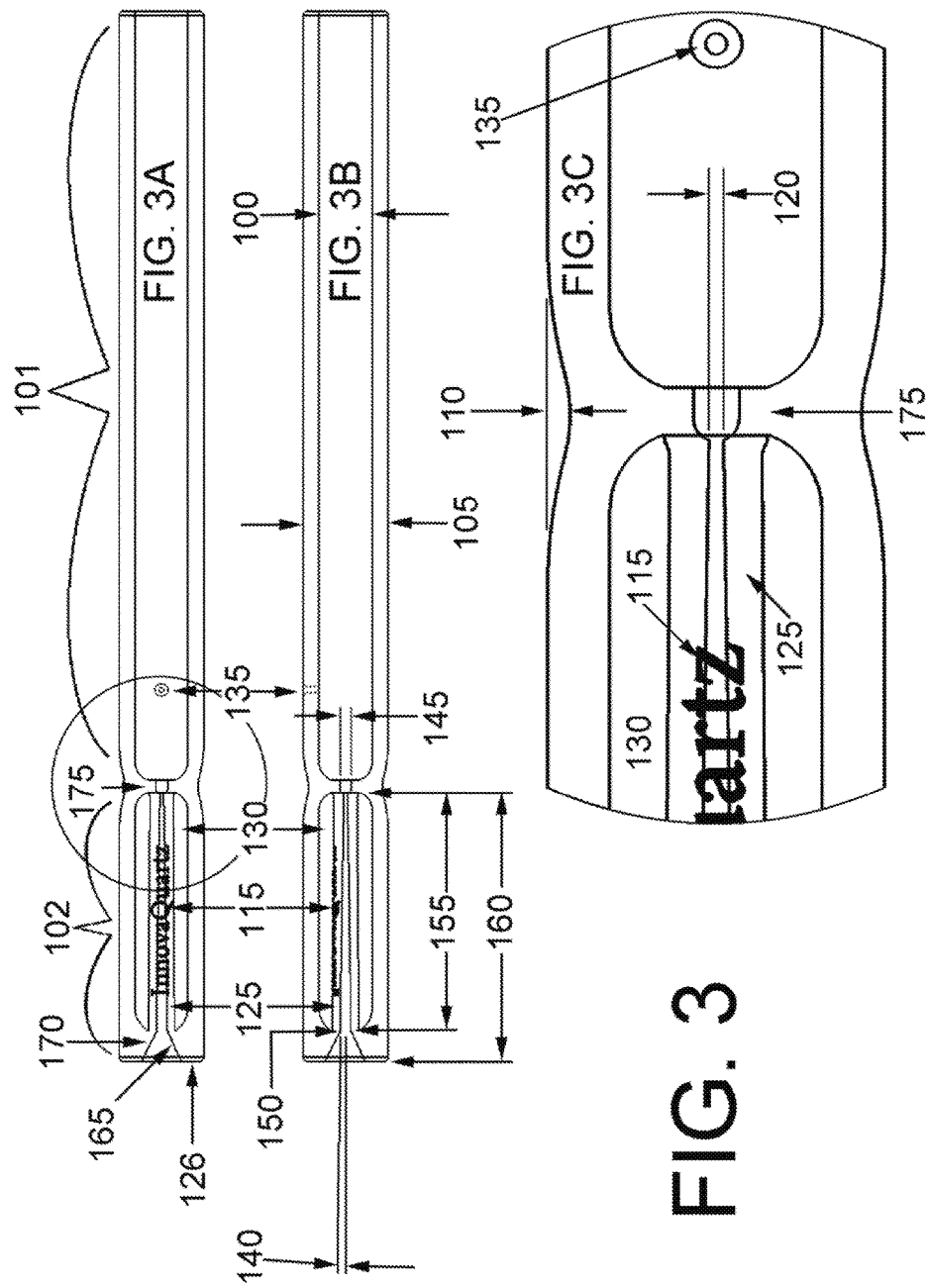

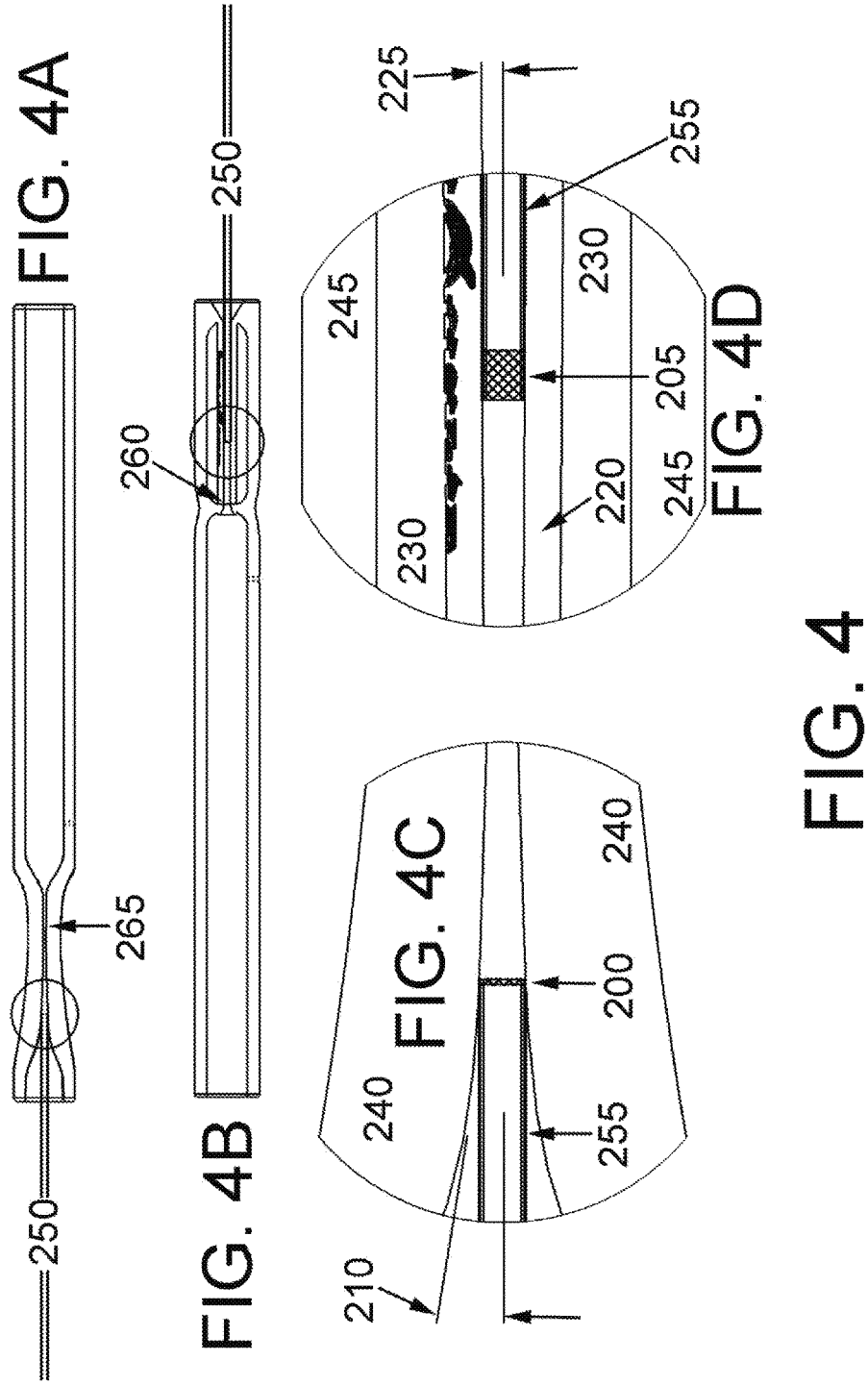

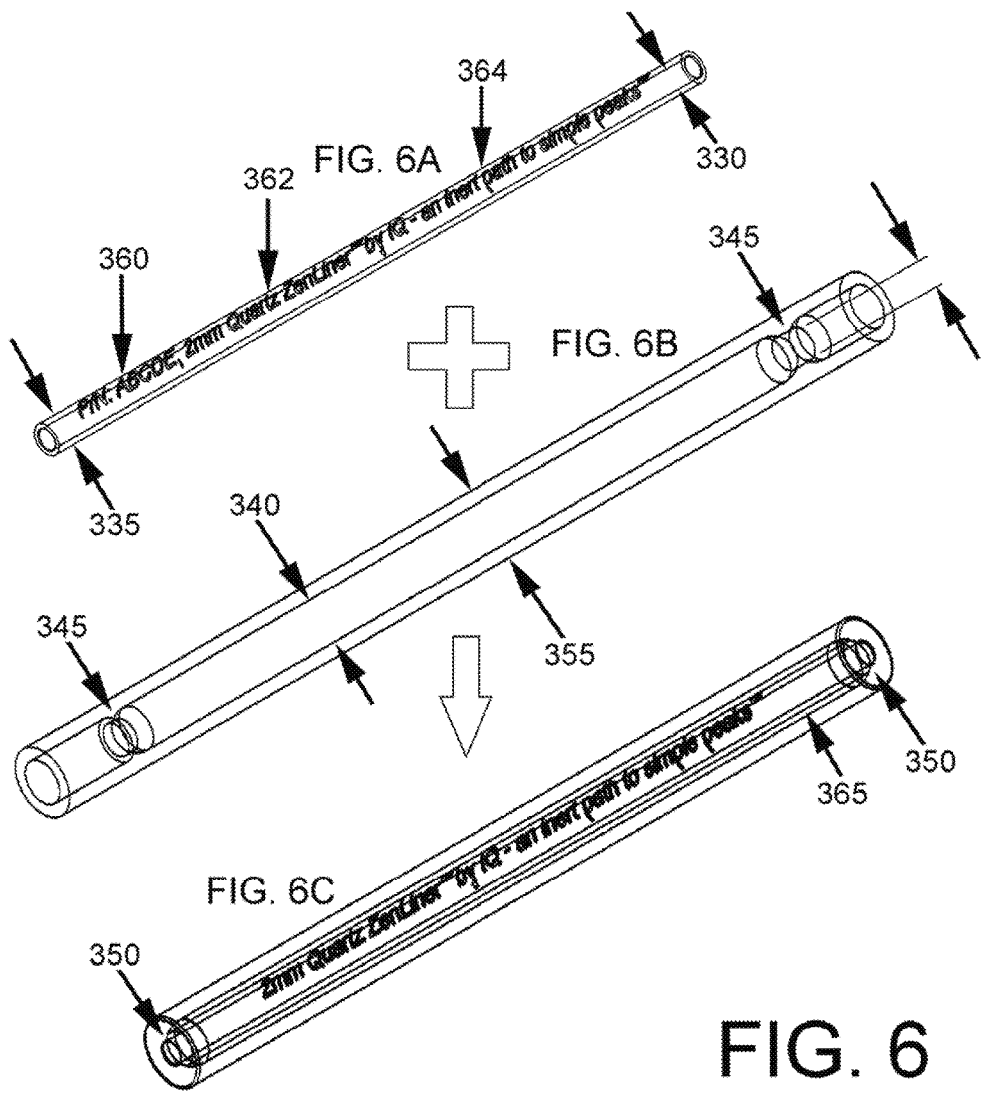

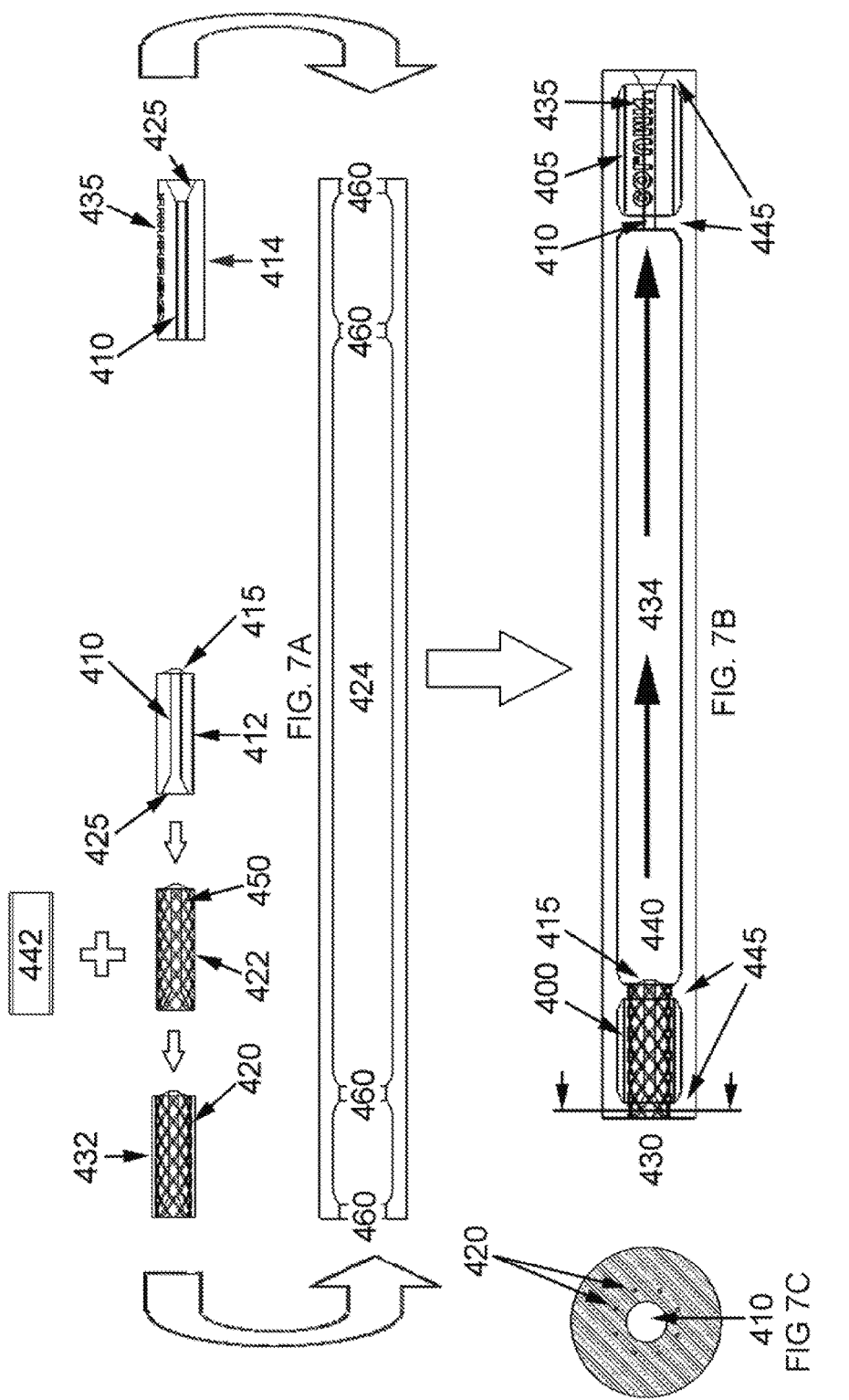

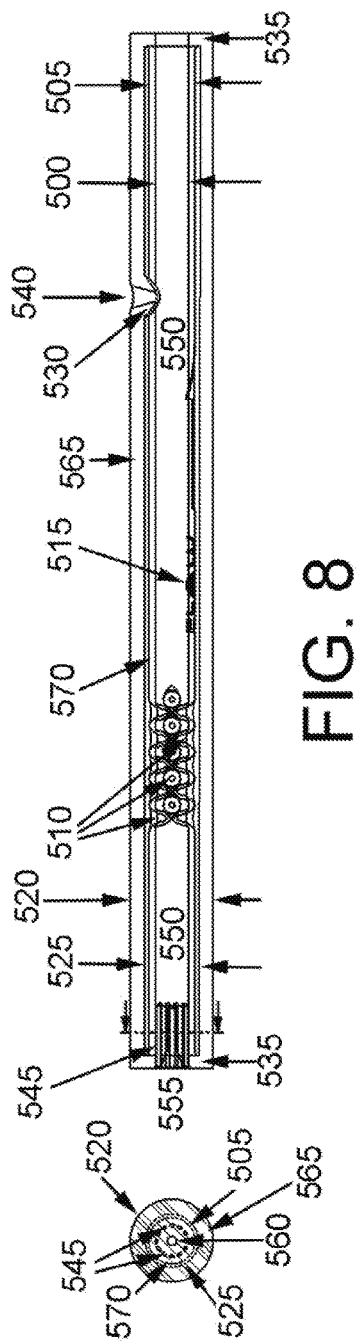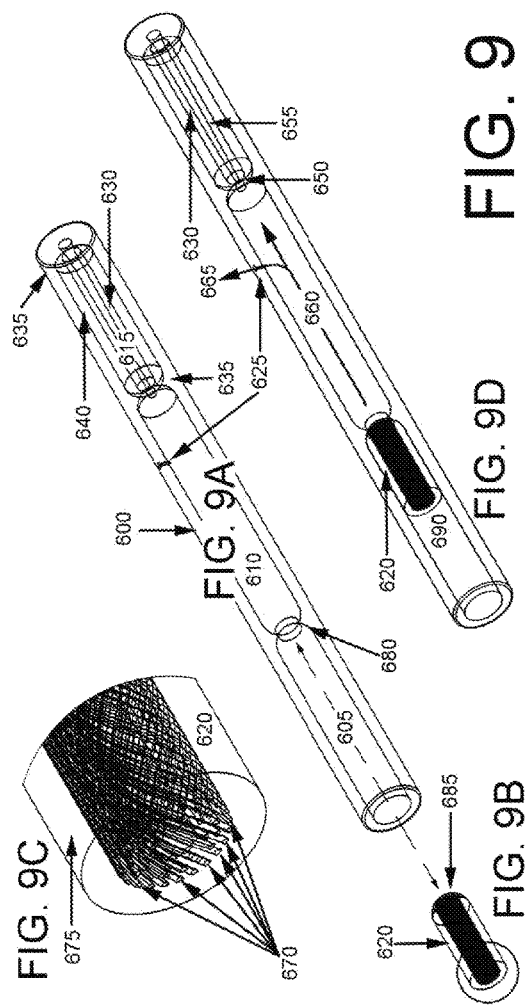

DOUBLE-WALL INLET LINERS FOR GAS CHROMATOGRAPHY

CROSS-REFERENCE TO RELATED APPLICATIONS

This disclosure claims the benefit of priority to U.S. Provisional Patent Application No. 62/242,279, filed 15 Oct. 2015, incorporated by reference herein in its entirety.

FIELD OF THE INVENTION

Double-walled injection port liners possessing thermochromic indicators and providing improved reproducibility for sample loading and reduced interferences in capillary gas chromatography.

BACKGROUND

Capillary gas chromatography (GC) is a widely used method for separation and identification of analytes, or derivatives thereof, that are stable in the gas phase. Samples are typically introduced to the instrument as liquids, by syringe injection through a rubber septum, into a glass-lined chamber within a heater block that is fixed to a wax-lined capillary column. The liquid sample vaporizes in the inlet liner, mixes with the carrier gas and all, or a portion, of the gaseous sample is swept onto the capillary column. Within the column different compounds dissolve in the thin, liquid, waxy stationary phase on the capillary wall to differing degrees and their progression through the column proceeds a different rates as a result. The outlet end of the capillary column is attached to a detector, e.g. a flame photometric detector.

A principle concern to the efficiency of GC is rapid and uniform sample vaporization and introduction to the column. A typical, split flow and direct injection sample vaporization chamber is shown in FIG. 1, where a heated block 1 houses an injection port liner 3. Injection port liners are most typically made of borosilicate glass for ease of heat-forming the conical restriction 7 (also known as a radial taper) within which a capillary separation column end 5 finds purchase at a taper diameter that approximately matches the capillary outer diameter. The liner 3 is also equipped with a vent 17 (e.g., a hole through the glass wall) for splitting off some of the vaporized sample flow.

Carrier gas is introduced through an inlet port 19 and flows as the dashed arrows indicate: into the open end 23 of the liner 3, about the needle 11 of the sample introduction syringe (not shown), with some flow continuing distally along the liner bore and into the open end 7 of the column 5 within the tapered restriction of liner bore while flow also splits, flowing through the vent 17, about the outer diameter of the liner 3 and out the split-flow exhaust port 21. The capillary column is traditionally held in its physical location by a Swagelok connector in the GC oven wall, represented by the graphite ferrule 15, and the liner is typically centered and sealed within the heater block 1 by a Viton O-ring 13 and graphite gasket 2.

The heated block 1 is typically heated to approximately 200° C. to 300° C. prior to sample introduction until the glass liner 3 is equilibrated with the block temperature. The sample is introduced by plunging the syringe needle 11, through a rubber septum 9 and depressing the syringe plunger (not shown), ejecting sample from the beveled needle tip 25. Ideally, the sample vaporizes immediately, filling the open area of the liner 3 with a uniform and representative solution of sample in carrier gas that is swept onto the column 5 opening 7 within the liner 3 conical taper. The amount of sample that is introduced to the column may be varied by controlling the carrier gas split flow via an adjustable flow restrictor in the exhaust port 21 or by other means.

Sample interactions with the inlet liner or sleeve surfaces are problematic but are considered unavoidable. The sample may degrade by interaction with the borosilicate glass or with constituents carried on the liner. Notably, liners are not replaced or cleaned after each use: as this would be prohibitively expensive in terms of liner costs and instrument downtime. Compounds from previous injections, reversibly absorbed to the inlet liner, can release and result in spurious peaks or baseline drift. Compounds that irreversibly absorb may become active or reactive sites for interactions with subsequently studied compounds or may degrade, producing spurious peaks.

Accordingly, borosilicate liners are almost universally coated to mask the intrinsic surface activity and reactivity. Common "deactivation" methods include reacting the exposed (surface) silanol with organosilane reagents (e.g., bis(trimethylsilyl)amine). Other treatments using gaseous silane and derivatives thereof have also proven effective but deactivation coatings are temporary and simply mask the underlying reactivity.

Additional adverse activity is often knowingly introduced by liner manufacturers in the form of markings on the liners, usually as enamel glazes that contain transition metals and other active and reactive functionalities. The markings are claimed to be necessary for "identifying and tracking liners" or "for proper installation orientation" or "positioning packing materials." While these markings are on the outer surface of the liner, the added activity and reactivity still interfere by way of diffusion of degradation products or reversibly absorbed compounds into the sample stream over time, particularly in split flow injection.

A less problematic method of marking liners has been glass etching or 'frosting', either by chemical or physical means. Etched surfaces are high in surface area (increasing total activity) and may be saturated with silanol groups, absorbed etching process contaminants, etc. and etching provides only low resolution such that the markings are typically large. Other purposed schemes for marking liners have also been proposed, e.g. U.S. Pat. No. 8,366,814 (Jones, et al.), proposes indicating compounds for visual determination of the liner temperature (for safety in hot swapping) or prior wear or abuse (potentially degraded deactivation due to exposure to excess temperature, oxygen or moisture, for example, and U.S. Pat. No. 8,999,044 (Rohland, et al.) proposes using color coding via use of colored glasses in liner construction.

SUMMARY

A first embodiment is an inlet liner for use within an injection port of a capillary gas chromatograph. The inlet liner including a body region affixed to a capillary column connector region; the capillary column connector region includes a first fused quartz tube having an inside surface, an outside surface, a length, the inside surface having a taper (half) angle of less than 1.5° and adapted to carry and/or affix to a termination of a gas chromatograph capillary column. The first fused quartz tube and the second fused quartz tube aligned along a common longitudinal axis with the outside surface of the first fused quartz tube affixed to an inside surface of the second fused quartz tube. The body region includes an evaporation and/or mixing volume in fluid communication with the inside surface of the first fused quartz tube.

A second embodiment is an inlet liner for use in a capillary gas chromatograph injection port, the inlet liner includes a first fused quartz tube having an outside surface; a second fused quartz tube having an inside surface. The first fused quartz tube and the second fused quartz tube aligned along a common longitudinal axis with the outside surface of the first fused quartz tube affixed to the inside surface of the second fused quartz tube at two points along the longitudinal axis thereby defining a hermetically sealed volume between the outside surface of the first quartz tube and the inside surface of the second fused quartz tube. The hermetically sealed volume entraining a reactive surface.

A third embodiment is an inlet liner that includes a sample injection section, a blending section, and a loading section, each in fluid communication; the loading section adapted to affix to a capillary gas chromatograph column; the blending section having a side vent and adapted to carry a sample and a carrier gas from the injection section, produce a split ratio of the sample and carrier gas, and deliver a portion of the sample and carrier gas to the loading section; the sample injection section carrying a filter segment; the filter segment includes a fused quartz monolith disposed therein, the fused quartz monolith includes a plurality of channels extending in open communication from an intake end of the fused quartz monolith to an output end of the fused quartz monolith.

A fourth embodiment is an installed inlet liner. The installed inlet liner includes an inlet liner that includes a first fused quartz tube having an inside surface, an outside surface, a length, the inside surface having a taper (half) angle of less than 1.5° and adapted to carry and/or affix to a gas chromatograph capillary column; the first fused quartz tube and the second fused quartz tube aligned along a common longitudinal axis; the outside surface of the first fused quartz tube affixed to an inside surface of the second fused quartz tube; a capillary gas chromatograph column, the column having a termination disposed within the inlet liner and adjacent to the inside surface; and a seal length that is the length of contact of the capillary gas chromatograph column measured from the termination.

BRIEF DESCRIPTION OF THE DRAWINGS

For a more complete understanding of the disclosure, reference should be made to the following detailed description and accompanying drawing figures wherein:

FIG. 2A depicts a typical direct injection inlet liner for gas chromatography in Agilent split/splitless ports, FIG. 2B is an enlargement of a portion of the liner.

FIG. 3A and FIG. 3B are different rotational depictions of a preferred embodiment of the invention for direct connection to capillary columns, FIG. 3C is an enlargement of a portion of this liner.

FIG. 4 compares prior art (FIG. 4A and FIG. 4C) to a preferred embodiment of the invention (FIG. 4B and FIG. 4D).

FIG. 6 is an isometric series of sketches depicting the assembly of a preferred embodiment of the invention, with two components, FIG. 6A and FIG. 6B, and finished product FIG. 6C shown.

FIG. 7 depicts the assembly of a preferred embodiment from four components and stages of that assembly FIG. 7A, with a cross-section FIG. 7C of the finished device FIG. 7B showing detail.

FIG. 8 depicts a preferred embodiment of the invention with a cross-section showing detail.

FIG. 9 illustrates a preferred embodiment of the invention FIG. 9D with an exploded view FIG. 9A and FIG. 9B illustrating replacement of an element of the liner and FIG. 9C showing detail of the replaceable element.

Figure 1:
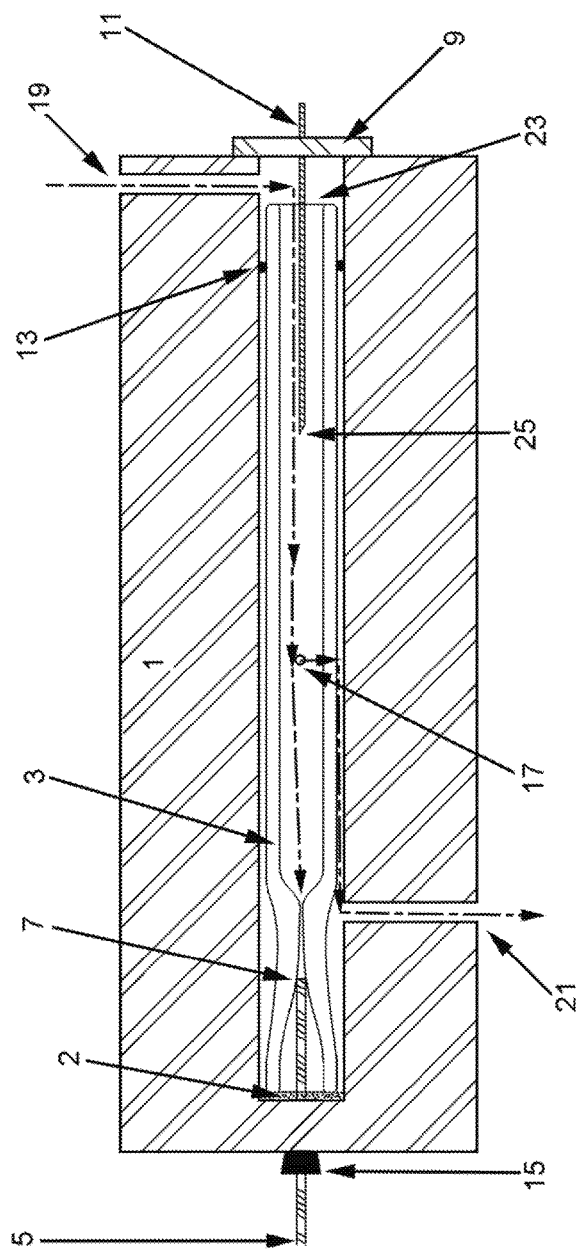
FIG. 1 is a cartoon of a simple injection port for liquid samples in gas chromatography.

While specific embodiments are illustrated in the figures, with the understanding that the disclosure is intended to be illustrative, these embodiments are not intended to limit the invention described and illustrated herein.

DETAILED DESCRIPTION

Herein are provided inert inlet liners, production methods, and strategies that provide completely inert marking for promotion, product identification, thermal history determination, and temperature indication. The herein provided inlet liners further offer improved dimensional reproducibility, reduced activity and reactivity, better thermal conductivity, higher heat capacity, superior thermal shock resistance, reduced susceptibility to physical damage, minimized sample carryover and relatively simple cleaning.

Standard GC liners are produced from borosilicate glass upon glassblowing lathes using traditional techniques. The Restek Uniliner™ liner depicted in FIG. 2 is no exception. A borosilicate glass cylinder, typically longer than the finished product length of approximately 78.5 mm, and having an internal diameter or bore 50 of approximately 4 mm and an outer diameter 55 or approximately 6.4 mm (slightly smaller for split flow injection and slightly larger for splitless injection), is rotated on a lathe and heated with a torch to form a press-fit type taper (also known as a conical bore or a radial taper) 70. The taper is produced by applying increasing amounts of heat as the flame moves from the column end 35 toward the inlet end 30, with differential heat usually produced through control of the flame traverse speed, and/or by stretching the tube as it is heated. The tube is then cut to length and the open ends 30 and 35 are flame polished. A vent hole 85 is bored with a glass drill for split flow applications.

Critical dimensions are inspected including the position 45 and dimension 65 of the restriction minimum (approximately 0.25 mm in the case of liners designed to accept a range of capillary columns), the taper length 70 (approximately 15 mm) and position within the liner 95, the vent 85 position (typically 51 mm from liner inlet 30, for bottom vented liners), breakout from drilling 90 and the minimum opening at the taper inception 60 of approximately 1 mm. The liner is then cleaned and typically marked with a part number and brand identification using ceramic inks applied by silk screen (or by decal transfer). Finally, liners are almost universally deactivated by some means.

The flame-formed, press-fit type tapers result in non-linear taper 70 or cones angles where the contact (half) angle 80 is typically much larger at the inception point 60 than it is near the diameter minimum 65; angles as high as 5° commonly result from flame-forming. Nonlinearity and waviness in the conical region 70 is even greater in the case of liners (as opposed to thinner wall unions and splitters) where the borosilicate glass wall is thicker and these tubes present high ovality, eccentricity, and dimension variation. Flame-formed, press-fit type liners further include a less obvious performance problem created by the reduction in outer diameter about the conical region 75; this distortion produces large dead volumes in the split flow region where compounds may collect and release over time, causing cross-contamination in the same or subsequent analyses. The significant region of reduced outer diameter is also in less intimate contact with the injection port heater block, reducing the efficiency of heat transfer. Further, the distortion from the variable cylindrical lens effect when viewing the conical bore from the outside complicates detection of gross errors in the cone angle 80 and renders determination of the locus of the taper minimum 65 and its actual diameter difficult within the required dimensional accuracy.

FIG. 3 depicts an alternative construction for a direct connect liner. In this embodiment, the inlet liner for use within an injection port of a capillary gas chromatograph can include a body region 101 affixed to a capillary column connector region 102. The capillary column connector region 102 preferably includes a first fused quartz tube 125 having an inside surface, an outside surface, and a length 160. The inside surface of the first fused quartz tube 125 preferably has a taper half angle 140 of less than 2°, 1.5°, 1.4°, 1.3°, 1.2°, 1.1°, 1°, 0.9°, 0.8°, or 0.7°. Herein a taper half angle is angle between the longitudinal axis of the fused quartz tube and a line segment on the inside wall of the fused quartz tube extending from the ID minimum to the ID maximum, commonly referred to herein as a 'taper' or 'tapered bore' or 'linear taper', the process for making which is disclosed in U.S. Pat. No. 5,512,078; an adaptation designed to carry and/or affix to a termination of a gas chromatograph capillary column. The capillary column connector region 102 further includes a second fused quartz tube having an inside surface, an outside surface, and an length. The first fused quartz tube 125 and the second fused quartz tube 126 aligned along a common longitudinal axis. The outside surface of the first fused quartz tube is affixed to an inside surface of the second fused quartz tube 126. Preferably, the length of the first fused quartz tube is equal to or less than the length of the second fused quartz tube. More preferably, an end of the first fused quartz tube does not extend beyond an end of the second fused quartz tube; even more preferably, both ends of the first fused quartz tube do not extend beyond the ends of the second fused quartz tube.

The body region 101 includes an evaporation and/or mixing volume in fluid communication with the inside surface of the first fused quartz tube 125. The body region includes an outside surface having an outside diameter. Preferably, the outside diameter of the body region and the outside diameter of the column connector region are the same. In one instance, the column connector region has an outside diameter that is commensurate with the outside surface of the second fused quartz tube. In a preferable example, the thermal fusion between the body region and the capillary column connector region includes a minimum deflection from the outside diameters of the adjoined regions. The deflection 110 is, preferably, less than 0.25, 0.3, 0.4, 0.5, 0.6, 0.7, 0.75, and/or 1 mm.

In one instance, the first fused quartz tube 125 is affixed to the second fused quartz tube 126 at two points 170, 175 along the longitudinal axis thereby defining a hermetically sealed volume 130 between the outside surface of the first quartz tube and the inside surface of the second fused quartz tube. In a separate instance, the inlet liner includes a thermal fusion 175 between the body region 101 and the capillary column connector region 102, wherein the inside surface of the first fused quartz tube has a minimum diameter 120 that is adjacent to the thermal fusion 175. As used here, the thermal fusion is the thermally treated (melted/softened) section of the tube between the respective regions, the thermal fusion can further be the point where two separate pieces are adjoined to form the line having the two regions (where, for example, the respective regions begin as separate pieces). In yet another instance, the inlet liner has a column insertion end, the column insertion end carrying an insertion chamfer 165 in fluid communication with the inside surface of the first fused quartz tube 126.

This embodiment can include a laser-formed, fused quartz, press fit union 125 supported or held within one end of the liner. As used here, the press fit union is the tube or portion of the tube that is adapted to affix to the gas chromatograph column by means of swaging upon the capillary coating within a narrowing bore or linear taper. This interior element possesses the bulk of the precision dimensions required for making the liner and offers far higher dimensional precision than is possible to produce directly upon liner tubing: quartz or borosilicate. The dimensional accuracy and precision, including eccentricity and ovality, that is available in laser-forming the press fit union 125 upon small diameter fused quartz offers a level of function for direct connect liners that has heretofore been unavailable in borosilicate liners. The taper (half) angle 140 is less than 2°, less than 1.5°, less than 1°, or preferably less than 0.9°, for all standard GC column diameters from 0.32 mm to 0.8 mm (polyimide outer diameter) as opposed to greater than 1° and up to 5° for the prior art. The tapered tube or the press fit union, preferably, has an eccentricity that is less than 0.5, 0.4, 0.3, 0.2, or 0.1, more preferably this eccentricity of the internal surface of the tube is less than 0.1, and even more preferably the eccentricity is zero. The tapered tube or press fit union, preferably, has a bore ovality that is less than 0.015 mm, 0.010 mm or 0.005 mm, and even more preferably the ovality of the tapered tube bore is zero.

The taper length 155 is longer and more precise than is possible to achieve in the flame-forming of the prior art. The minimum opening at the taper maximum 150 is held to ±0.03 mm as opposed to ±0.5 mm in prior art. Herein, the taper minimum diameter 120 is larger (for example, 0.275 mm versus 0.25 mm yielding less restriction to sample flow), more precise (for example, ±0.025 mm versus ±0.05 mm yielding more reproducible sample loading) and its locus 160 is far more reproducible (for example, ±0.5 mm versus ±3 mm) yielding more reproducible thermal conditions in the column terminus. The column insertion chamfer 165 or insertion guide is smooth and linear to reduce the risk of chipping the column on insertion where the sole guide is tactile. Preferably, the tube 125 has an internal surface that tapers from a maximum internal diameter at a column insertion chamfer to a minimum at or near a connection to a body region. The taper half angle is, preferably, less than 1.5°, 1.4°, 1.3°, 1.2°, 1.1°, 1°, 0.9°, 0.8°, or 0.7°. More preferably, the internal surface maintains an eccentricity, along a length of the tube, that is less than 0.1, even more preferably, less than 0.05. Even more preferably, the tube 125 has an ovality at all points along the tube that is less than 5%, even more preferably, less than 2.5%.

Columns are loaded into direct connect liners for instruments blindly, after the liner has been installed in the injection port. Access to the direct connect taper is gained through the GC oven wall, via a bulkhead capillary connector, e.g. a compression or SwageLok®-type fitting. It is impossible to inspect the seal between the column and the liner after installation, whereas visual inspection is fundamental for insuring there are no leaks when using press fit type connectors anywhere in the GC sample path. A reliable press fit taper seal is essential to the reproducible performance of such column installations; tailing peaks, spurious peaks, and drifting baselines may result from a cracked column end or an otherwise bad seal and these defects are not detectible until the problems present themselves during analyses.

Figure 10:
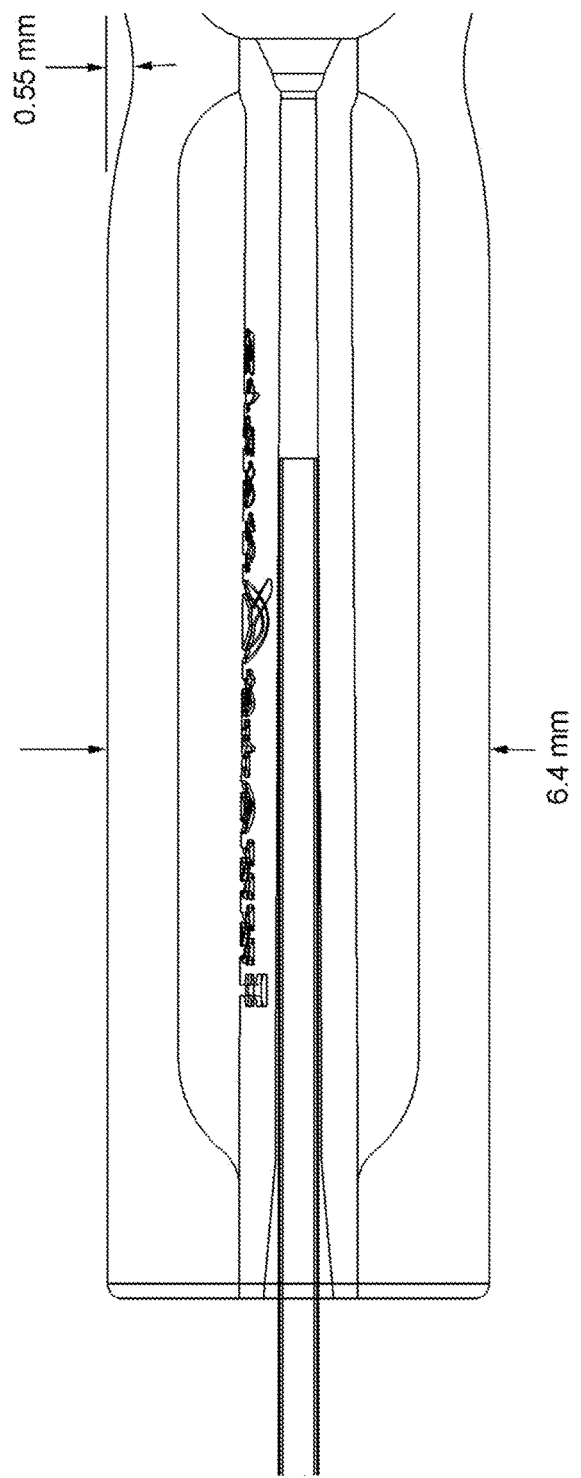
FIG. 10 is a photograph of a capillary column installed within an inlet liner.

Press fit type seals are produced by compression of a thin layer of polyimide—0.015 mm to 0.030 mm thick—between the thin-walled fused silica capillary—typically less than 0.05 mm glass thickness—and the press fit taper wall. FIG. 10 shows the compressed thin layer of polyimide (seal) for a adjoined GC column and a press fit taper wall.

The compressed polyimide is observable under magnification (for press fit unions and Y splitters) as a darker color due to the exclusion of air between the glass and polyimide. The angle of contact between the capillary and the press fit taper determines the length of the polyimide coating that is compressed; high angles provide short seals where low angles provide long seals. Further, where taper half angles are too high, e.g., above 3°, the glass of the capillary may come into contact with the press fit taper wall, scoring the wall (exposing untreated glass) and chipping or cracking the capillary at the opening.

Chipping and cracking a column end can lead to catastrophic failure. Cracks often propagate axially along the column length due to lines of stress concentration where capillary is drawn too quickly or too cold. Chips that enter the capillary may be driven deep within the column by the gas flow that transports the sample. Even small chips of glass that bound off the column wall cause damage that leads to extreme fragility in the entire affected column length. Instructions for installing columns within direct connect liners caution against chipping the column and even require pre-compression of the ferrule (15 in FIG. 1) about the column before fully inserting the column into the liner least the slight forward pressure resulting from ferrule distortion in initial tightening produce sufficient force to crush the capillary within the liner press fit taper.

A 5° press fit half angle provides roughly 0.1 mm of compressed polyimide length 200 (in FIG. 4) behind the column opening. Column cut ends are rarely orthogonal to the column axis and irregularities often exceed the 0.1 mm seal length such that only part of the column circumference is sealed in high angle tapers. Herein, a press fit union 205 affixed to a column can include a seal (i.e., compressed polyimide) that has a length of about 0.2 mm, 0.25 mm, 0.3 mm, 0.35 mm, 0.4 mm, 0.45 mm, 0.5 mm, 0.55 mm, 0.6 mm, 0.65 mm, 0.7 mm, 0.75 mm, or 0.8 mm, thereby even very poorly cut columns form gas-tight seals. Preferably, the seal length is about 0.25 mm to about 0.6 mm, about 0.25 mm to about 0.5 mm. Further, with a taper half angle of less than 1°, pressure due to tightening the bulkhead column connector serves only to improve the seal with no risk of crushing the capillary; therefore installation is simplified and secure.

By way of a specific example, the embodiment shown in FIG. 3 can be produced by fusing a 2 mm outer diameter press fit union 125 within a 4 mm liner bore 100 at the column insertion end 170 and at a position 21 mm higher within the liner 175. The process can include first collapsing the inner diameter 100 of the liner tube under rotation (and with optional compression to minimize deformation of the outer diameter 105, as depicted by 110) and with $CO_2$ laser heating until the restrictions are slightly larger than the press fit union 125 outer diameter. The press fit union 125 is then positioned within the restrictions and heat is again applied at 170 and 175, fusing the half union within the liner bore and producing a hermetically sealed space 130 about the union section. Preferably, the deformation in the outer diameter is less than 20%, 10%, 9%, 8%, 7%, 6%, 5% of the outside diameter of the liner tube. More preferably, the outer diameter at the fusion 175 is about 0.05, 0.1, 0.15, 0.2, 0.25, 0.3, 0.35, 0.4, 0.5, 0.75, 1 mm less than the outer diameter of the liner tube. Still further, the deformation in the outer diameter is preferably less than about 0.4, 0.5, 0.6, 0.7, 0.75, or 1 mm.

The hermetically sealed area 130, provided herein, affords a marked liner 115 without an increase in activity or reactivity ascribed to etching or markings. In one instance, the lettering can be engraved upon the half union and the recessed lettering is optionally filled with an ink or thermochromic glaze prior to inserting it into the liner for fusion. For example a glaze that changes color when the liner is exposed to temperatures that are damaging to the deactivation coating, or a glaze that presents a characteristic warning color when the liner is hot enough to cause a spontaneous pain response of releasing the hot item (to fall and shatter on the laboratory floor).

Markings produced on prior art liners are exposed to sample in split flow injections and, as such, may degrade or bind sample components and later release them as cross contaminants. A part number, lot number or bar code may also be produced in place of, or in addition to, the brand identification of this example, with zero risk of cross-contamination.

Additional improvements to liner performance result from a direct connect liner made of or consisting of fused quartz. Preferably, wherein the surfaces in fluid contact with samples of carrier gas(es) consist of fused quartz; more preferably, wherein the surfaces are polished fused quartz (i.e., polished surfaces are free of etching or intentional pitting in the fused quartz surface).

More reproducible injections result from more reproducible and more favorable dimensions about the column opening. Flame-formed tapers in borosilicate liners do not provide taper minima directly at the specified endpoint for the taper; there is typically a portion of increasing diameter beyond the minimum as may be seen beyond the minimum 45 in FIG. 2. Prior art permits a restriction as small as 0.2 mm diameter and up to 0.45 mm diameter to pass sample onto up to a 0.53 mm bore column, and the location of the minimum is even more variable, resulting in a wide range of possible flows for a single model of liner; injection to injection reproducibility is poor and liner to liner reproducibility is abysmal. The taper minimum described herein has very reproducible dimensions and the locus reproducibly occurs very close to the sample entry where entry is further facilitated by the larger bubble diameter 145.

Injecting liquid samples onto liners rapidly, as is required for GC, cools the liner bore surface due to the latent heat of vaporization of the solvent and sample constituents. Herein, the insulation effect of the Dewar-like barrel about the column connection within the new art liner acts to dampen thermal cycling that weakens the column to liner connection within the prior art, particularly in reverse installation where the injection needle places sample directly within the column opening (embodiment not shown).

A further improvement to direct connect liners is illustrated in FIG. 4: FIG. 4A shows a standard Restek (Agilent compatible) direct connect liner with a detail of the column connection region provided in FIG. 4C. The darkened band 200 indicating the seal length for the prior art is short due to the high half angle of contact 210 between the polyimide 255 and the press fit wall 240 of the liner.

FIG. 4B shows a direct connect liner for, for example, a 0.53 mm bore column 250 where the column connection detail is provided in FIG. 4D. The taper half angle 225 is, preferably, less lower than 1°, 0.5° or 0.4°, resulting in a very long seal 205 owing to a larger taper minimum 260, e.g., of 0.575±0.025 mm for the column (diameter) specific insert 220 versus the prior art minimum 265 (0.2+0.25/−0 mm). The hermetically sealed portion can include a partial vacuum 230 between the press fit union half 220 and the liner wall 245, serving to maintain the integrity of the seal 205 in thermal cycling. The large taper minimum 260 presents no restriction to gaseous sample access (simple direct connect split flow injections) or for needle access in cold, on-column injections.

FIG. 4B shows a capillary column installed within an inlet liner as it is in use. This installed inlet liner includes the inlet liner affixed to a capillary GC column with a seal length greater than, for example, about 0.2 mm. Herein, the seal length is the length of contact between the GC column and the inlet liner, in one instance this is the length or amount of compressed polyimide coating that is carried on the outside surface of the capillary column, in another instance this is the length of contact between the GC column and the inside surface (fused quartz) of the inlet liner.

Preferably, the installed inlet liner has an inlet liner that includes a first fused quartz tube having an inside surface, an outside surface, a length, the inside surface having a taper angle of less than 1.5°, or 1° and adapted to carry and/or affix to a gas chromatograph capillary column. The first fused quartz tube and the second fused quartz tube are preferably aligned along a common longitudinal axis and the outside surface of the first fused quartz tube affixed to an inside surface of the second fused quartz tube. The installed inlet liner further includes a capillary gas chromatograph column, the column having a termination disposed within the inlet liner and adjacent to the inside surface. In a preferred instance, the installed inlet liner includes a seal length that is the length of contact of the capillary gas chromatograph column measured from the termination. In one instance, the seal length is greater than about 0.25 mm. In another instance, the seal length is greater than 0.3 mm, greater than 0.4 mm, or greater than 0.5 mm. In another instance, the internal diameter is 0.275±0.025 mm, 0.400±0.025 mm or 0.575±0.025 mm.

Figure 5B:
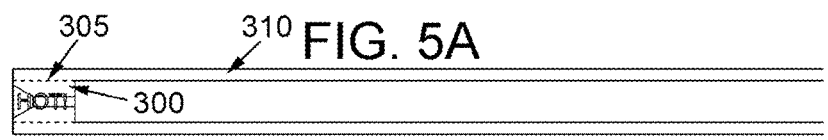
FIG. 5 depicts an embodiment of the invention where the outer diameter of a liner taper element is laser engraved prior to fusion within a liner body, leaving voids that remain legible after fusion, as a cartoon FIG. 5A and as a photo FIG. 5B.
Figure 5:
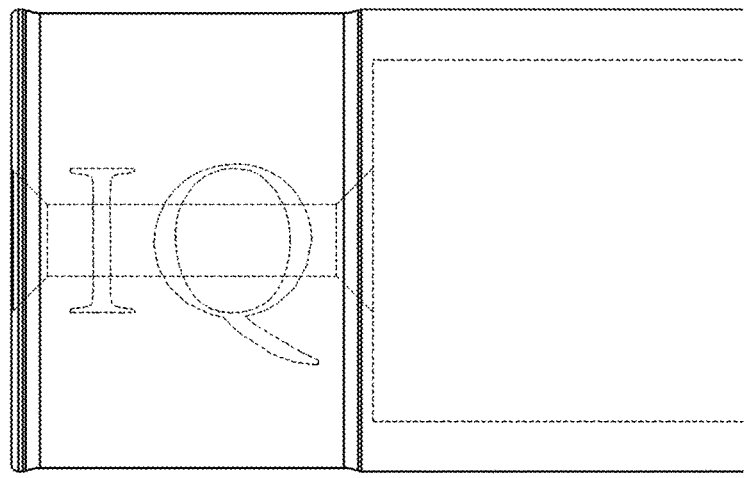

Alphanumeric or bar code information need not be combined with thermochromic information, and vice versa, and Dewar-like barrels need not be present to permit zero activity markings, thermal or otherwise, as shown in the FIG. 5A and photo 5B, where the letters 'HOT!' (5A) or 'IQ' (5B) are produced upon the outer diameter of a 4 mm insert 300 fused 305 within a 4 mm bore liner blank 310. Thermochromic material need not be limited to those available as enamels or inks nor need they be restricted to filling recesses provided by lettering or bar code grooves; colorants and indicators may be added in any form, as granules, coated glass beads, or gases within the hermetically sealed spaces provided by the construction strategy disclosed.

The double-walled construction strategy is not limited to direct connect type liners. So called gooseneck or taper liners, spiral mixer and spiral splitter liners, flow reversal cup liners and even straight liners may be made by the same technique as described for the direct connect liners. Beginning with the simplest liner of all, another embodiment of a straight tube liner is depicted in FIG. 6. This embodiment of an inlet liner for use in a capillary gas chromatograph injection port can include a first fused quartz tube having an outside surface. The inlet liner further includes a second fused quartz tube having an inside surface. The first fused quartz tube and the second fused quartz tube are aligned along a common longitudinal axis and the outside surface of the first fused quartz tube is affixed to the inside surface of the second fused quartz tube at two points along the longitudinal axis thereby defining a hermetically sealed volume between the outside surface of the first quartz tube and the inside surface of the second fused quartz tube. Preferably, the hermetically sealed volume entrains a reactive surface.

In one instance, the reactive surface is a marking carried on the outside surface of the first fused quartz tube and within the hermetically sealed volume. This marking can be selected from an etching on the outside surface of the first fused quartz tube, an enamel, a thermochromic material, a thermochromic material carried within an etching on the outside surface of the first fused quartz tube, and an enamel carried within an etching on the outside surface of the first fused quartz tube. In another instance, the reactive surface is carried on a heat conducting material entrained within the hermetically sealed volume. The heat conducting material can be selected from copper power, copper beads, aluminum powder, aluminum beads, and a fusible alloy. In one example, the fusible alloy has a composition that includes bismuth and/or tin. In another example, the fusible alloy has a composition that includes In, Ga, and Sn. In still another instance, the length of the second fused quartz tube is greater than the length of the first fused quartz tube. For example, the second fused quartz tube can extend beyond one end of the first fused quartz tube and be flush with the second end. In still yet another instance, the first fused quartz tube is thermally fused to the second fused quartz tube; preferably, the two fused quartz tubes are thermally combined to yield a unitary, fused-quartz piece. Notably and as used herein, fused quartz is distinguishable from two pieces fused together, fused quartz is a definition of a composition whereas thermally fused or fused pieces refer to the result of a process wherein a material is converted to a fluid state, joined to a second material, and cooled yielding weld, joint, or bond between the two materials; preferably, herein, the two materials are fused quartz and the fused pieces form a unitary structure that is composed of fused quartz.

In FIG. 6, a precisely dimensioned fused quartz tube 6A with, for example, a 2 mm bore 335 and 3 mm outer diameter 330 is laser engraved with a part number 360, a product name 362, and a marketing slogan 364. The character pockets are, optionally, filled with colorants that can have one or more functions, including: contrast for legibility, thermochromic indication of current temperature and thermochromic indication of thermal history. A larger tube, for example, having a 4 mm bore 340, a 6.4 mm outer diameter 355, and a length longer than the final functional length (e.g., 78.5 mm), is equipped with two melt restrictions 345 that are spaced at, for example, approximately 78.5 mm, center-to-center, where the inner diameter of the liner blank is reduced to just larger than 3 mm.

The marked, 2 mm by 3 mm, tube is placed within the larger tube such that the ends of the small tube align with the melt restriction centers and the restrictions are again heated, producing a fusion seal 350 at both ends. The in-process liner is then cut to length and the ends are polished, preferably laser cut and polished for low activity, yielding a double-walled (2 mm) bore liner with product identifiers, advertising and thermochromic indicators 6C. The liner is cleaned and inspected before deactivation (if any).

While any advantage for producing a Dewar-like 2 mm or other inside diameter straight bore liners may appear limited to enabling the inert marking or thermochromic indicator(s), other performance advantages include greater precision and greater accuracy in the liner volume and improved heat transfer uniformity. Heavy-wall fused quartz tubing is needed for producing small bore liners for Agilent and some other GC instruments, straight or otherwise (and other instruments presenting large bore injection port heater blocks). Dimensional control in drawing (manufacturing) large, heavy wall borosilicate and quartz tubing is poor (without adding great expense through sorting) due to limitations in the precision and accuracy of the required preform tubes but smaller diameter, relatively thin wall tubing may be very tightly controlled at essentially no additional cost and at far lower cost than the heavy walled tubes or prior art. Accordingly, double-walled liners such as those disclosed may be produced with far greater reproducibility of internal dimensions than prior art single wall liners without additional expense.

The hermetically sealed volume or void 365 of the double wall liner can be filled with a heat conducting material for faster heat transfer, shortening warm-up times and affecting more reproducible vaporization of injected samples (e.g. liquid metal eutectic or copper beads).

FIG. 7B depicts a double taper liner embodiment showing solid arrows indicating the direction of gas and sample flow. This example provides reduced flashback onto the septum (top taper 400) or onto the bottom seal (bottom taper 405), or both (in case of double taper liners), thereby reducing deposits of sample contaminants that degrade or slowly release or are inadvertently introduced by subsequent passages of the sample syringe needle (carrying deposits on the septum into the liner). Particularly where a sample 'explosively' vaporizes, it useful to produce smaller ports 410, a volcano like flare 415 about the top port opening (to discourage back flow) and provide off-axis helical channels 420 as alternative pathways for flashback.

The embodiment in FIG. 7 can be produced by first making taper inserts 412 and 414, beginning with tubes having the same or similar bore (chosen to be larger than the largest column diameter at the bottom end 414 and chosen to be larger than the largest sample needle at the top end 412) but differing in outer diameter by approximately a half millimeter. Then both taper inserts are chamfered 425 and the bottom insert 414 can be laser engraved "COLUMN" 435 (or "BOTTOM" or with an arrow defining the gas flow direction, etc., for orientation in installation) and, optionally, filled with thermochromic indicator in the engraved voids. (Column end taper inserts 414 are often longer than needle end tapers because columns are loaded blindly and it is undesirable for the column end to extend past the end of the insert.)

The top end taper insert can be similarly equipped with a volcano like face 415 to discourage back splashed sample (or flashback) from entering the needle guide and a series of small, helical grooves 450 are machined on the outer diameter of the approximately 0.5 mm smaller tube segment 412, producing 422. A thin walled tube 442 is placed about 422 and fused in place to produce helical channels 420 in the wall of the top taper insert 432 providing communication between the septum side 430 and the inside 440 of the liner 434 following assembly.

A prepared liner housing blank 424 can have four pinch points 460—circumferential restrictions produced by heating the tube under rotation—that are slightly larger in bore than the outer diameters of the two inserts. The inserts 414 and 434 are disposed within the liner blank bore at the restrictions and the restrictions are re-hearted to cause the two close-fitting surfaces to merge, retaining the inserts in place 445 at both ends and producing the double taper liner depicted in FIG. 7B. FIG. 7C provides a cross-section very close to the input end of the liner, showing the accessory vents 420 provided in the improved input taper of the embodiment.

In use, flashback can often be dominated by the Leidenfrost effect, where droplets of liquid sample dance about on the heated surfaces propelled by a vapor layer. The embodiment depicted in FIG. 7 finds particularly advantages in such cases by providing multiple pathways for pressure relief and relatively long and narrow channels that limit droplet movement and force vaporization to occur before droplets can contact and absorb to the septum.

In yet another embodiment, improved mixing of injected samples with carrier gas can be provided. Previously, liners like the famed Walter Jennings' cup splitter (U.S. Pat. No. 4,035,168, Jennings) and spiral insert splitters like Restek's Cyclosplitter™ (U.S. Pat. No. 5,119,669, Silvas, et al.) were designed to overcome the activity problems of glass wool plug liners that were used to combat the Leidenfrost effect. Notably, the prior art does not solve the problem of particles of septa collecting in areas that are difficult (latter) or impossible (former) to clean and where the contaminated liners are too costly to simply discard. For example, Agilent has extended the basic dimpled liner designs of Joint Analytical Systems (U.S. Pat. No. 6,929,780, Gerstel), developed and first produced in our laboratory in the 1990s, for replacing the Jennings and Silvas devices on the grounds that they are more easily cleaned and do not harbor particles within sample flow volumes (U.S. Pat. No. 8,713,989, Pa, et al.), but at a cost of a highly irregular outer diameter that provides myriad deep dead volume pits for harboring split flow waste, similar to the problems discussed for prior at FIG. 2.

Herein, FIG. 8 depicts an embodiment that corrects the deficiencies in the designs disclosed in Pa '989. This embodiment provides a tortuous path and maintains the constant outer diameter of the liner (owing to the double-wall construction strategy). Altering the outer diameter of the liner with deep dimples, as in Pa '989, reduces the efficiency of heat conduction between the liner and the heater block of the injection port and provides multiple, small dead volumes within the split flow volume for harboring compounds from prior split flow injections that may lead to cross-contamination between separations.

The herein disclosed embodiment provides a smaller dimpled tube that is then housed within a standard liner blank with an unblemished outer diameter. The precisely dimensioned smaller tube 570 has an inner diameter 500 and an outer diameter 505 where the outer diameter is substantially smaller than the inner diameter 525 of the liner housing blank 565. The inner tube 570 can be decorated with rows of overlapping dimples 510, as in the prior art, and is preferably equipped with a vented taper insert having a port 560 slightly larger than the sample needle. As shown in the FIG. 8, the embodiment can include axial vent channels 545 encircle the port 560 and provide fluidic communication between the liner bore 550 and the volume 555 about the septum (not shown).

In one instance, the smaller, dimpled tube 570 is laser engraved 515, in this case with an arrow indicating the direction of flow, and may be provide with thermochromic indicator as discussed above. The inner wall 525 of the liner outer tube 565 is spot fused to the outer wall of the inner dimpled tube 570 at 530 following fusion at the liner ends 535 (as previously described) to permit a laser puncture 540 where provision for a split flow is desired (vent hole providing fluidic communication between the liner bore 550)

Liners get dirty; as long as rubber septa serve as the penetrable barrier between the laboratory and carrier gas/sample mixing, this will remain a fact of life for chromatographers. If the steep upward trend in heavy petroleum production continues, among other trends, the need to analyze dirty samples will also grow. Current liners for dirty samples remain challenging to clean regardless of the claims of the designers. In another embodiment, a new liner design offers a means of replacing the filter (akin to prior art glass wool plug liners) but without the increased activity of the glass wool itself and without the irreproducible packing density and packing position which are inherent with glass wool plugs. FIG. 9 depicts a preferred example of an inlet liner with a replaceable filter segment.

In yet another embodiment, the inlet liner can include a sample injection section 605, a blending section 610, and a loading section 615, each in fluid communication. The loading section 615 can be adapted to affix to a capillary gas chromatograph column, for example by employing the press fit couplings described above and shown in, for example, FIG. 3. Alternatively, the loading section can loosely accommodate the capillary column, as in FIG. 7. The blending section 610 may contain a side vent 625 adapted to carry a sample and a carrier gas from the injection section 605, produce a split ratio of the sample and carrier gas, and deliver a portion of the sample and carrier gas to the loading section 615. The blending section may be a simple chamber, as illustrated or alternatively it may include dimples as depicted in FIG. 8 or some other mixing element such as multiple and parallel helical channels (so-called 'cyclo' mixers), nested cups, etc. The sample injection section 605, preferably, carries a filter segment. The filter segment can include a fused quartz monolith 620 disposed therein, the fused quartz monolith 620 includes a plurality of cannels 670 extending in open communication from an intake end of the fused quartz monolith 620 to an output end of the fused quartz monolith. Preferably, the filter segment is removably disposed within the sample injection section 605. In one example, the inlet liner includes a constriction 680 in an internal surface between the sample injection section 605 and the blending section 610. Preferably, the filter segment rests upon the constriction 680; and prevents the filter segment from entering the blending section 610. The internal surface of the constriction 680 and the external surface of the filter section 685 are, preferably, matched to provide a concentric seal, thereby providing a flow path from the sample injection section to the blending section through the plurality of channels 670 and not around the filter section. More preferably, the sample injection section 605 includes an open end distal from the fluid communication to the blending section 610 and the filter segment is sized and shaped to be removable through the open end of the sample injection section 605.

In another example, the reusable, direct connect liner body 600 has three functional sections: a sample injection, filtration and vaporization section 605, a blending and flow split section 610 and a sample loading section 615. FIG. 9A depicts the liner as it is within the instrument with the replaceable filter segment 620 seated at the bottom of the first functional section of the liner. For instruments with vertical injection ports like the HP 5890 and Agilent 6890, gravity and gas flow are sufficient for retaining the filter 620 in place.

The filter, in this case (detail FIG. 9C), is a fused quartz tube 675 that is produced in layers beginning with a rod (or capillary) upon which grooves are laser engraved in a gentle helix, as described in U.S. Pat. No. 7,469,557 (Griffin, et al.), incorporated herein in its entirety by reference. A thin-walled tube of quartz is disposed over the grooved rod and fused to the original outer diameter and the new outer diameter is laser engraved with helical grooves with a proportionately gentler helical path (to insure the lengths of the second layer of grooves matches the first set). A third tube is disposed over the new diameter and fused, etc. until the filter blank 620 has been constructed. The filter is then sectioned and shaped 685 appropriately to mate with an interior surface 680 of the liner body 600 as illustrated by the small, dashed arrow.

Sample injected into the liner at 690 is driven onto the filter's channels 670 (as either liquid or gas) by carrier gas flow where the high surface area of the filter element 620 vaporizes the sample and initiates blending with carrier gas. The volatilized sample enters the blending chamber 610 (shown here as a simple cylindrical volume, but other blending elements are possible), following the average path shown by arrow 660, then splitting the flow through the laser formed side vent 625 (providing fluidic communication between the blend chamber 610 volume and the split flow volume 665 outside the liner—refer to FIG. 1).

A portion of the blended sample enters the sample loading section 615 at 650, where the diameter of the port 650 is larger than the diameter of the capillary column (not shown, see FIG. 4D). The sample loading section can include the above described column-specific connector 630 having a taper half angle of less than 1.5° 655. The connector 630 is fused 635 within two restrictions produced within the liner blank similar to the method described for FIG. 7.

As septum particles collect on the input face of the filter element 620, as detected by visual inspection or performance degradation, the filter may be replace with a new filter segment to restore performance, immediately, or the liner may be removed from service while the filter element is cleaned. In most cases, cleaning will involve removing the filter element 620 and wiping the face with a solvent compatible with the deactivation coating, if any. In some cases, where particles are smaller than the openings of the sieve channels 670, back-flow of solvent may be required. If no deactivation coating is applied to the filter element, flash combustion in a muffle furnace will consume all organic contaminates. In another example, thermochromic indicators for current temperature can be positioned under the outer layer of quartz in the filter element. Notably, in practice, the filter element may remain hot significantly longer than the outer diameter of the liner body 600.

Cup and spiral splitters similarly may be constructed with the advantages of double wall design, through similar modifications to the functional elements for which they are named (as described herein for taper segments and direct connect segments), or simply by adding standard splitter and cup elements within single taper, double taper and direct connect designs previously discussed. Even frit liners are amenable to improvement by applications of the disclosed invention.

Those skilled in the art will recognize the potential for producing a second fluidic pathway connecting to the liner annular volume to produce an internal, fluid or gas heated liner, or embedding heating coils, RF receiver coils or other microwave absorbing material within the available space to produce light weight, miniature and rapid response injection ports. Alternatively, the annular space may be tasked as the sample vaporization volume with a cartridge heater or heated fluid flow within what is traditionally the liner bore.

Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

What is claimed:

1. An inlet liner for use in a capillary gas chromatograph injection port, the inlet liner comprising:
    a first fused quartz tube having an outside surface;
    a second fused quartz tube having an inside surface;
    the first fused quartz tube and the second fused quartz tube aligned along a common longitudinal axis;
    the outside surface of the first fused quartz tube affixed to the inside surface of the second fused quartz tube at two points along the longitudinal axis thereby defining a hermetically sealed volume between the outside surface of the first quartz tube and the inside surface of the second fused quartz tube, the hermetically sealed volume entraining a reactive surface.

2. The inlet liner of claim 1, wherein the reactive surface is a marking carried on the outside surface of the first fused quartz tube and within the hermetically sealed volume.

3. The inlet liner of claim 2, wherein the marking is selected from an etching on the outside surface of the first fused quartz tube, an enamel, a thermochromic material, a thermochromic material carried within an etching on the outside surface of the first fused quartz tube, and an enamel carried within an etching on the outside surface of the first fused quartz tube.

4. The inlet liner of claim 1, wherein the reactive surface is carried on a heat conducting material entrained within the hermetically sealed volume.

5. The inlet liner of claim 4, wherein the heat conducting material is selected from copper power, copper beads, aluminum powder, aluminum beads, and a fusible alloy.

6. The inlet liner of claim 5, wherein the fusible alloy has a composition that includes bismuth and tin.

7. The inlet liner of claim 1, wherein a length of the second fused quartz tube is greater than a length of the first fused quartz tube.

8. The inlet liner of claim 1, wherein the first fused quartz tube is thermally fused to the second fused quartz tube.

* * * * *